United States Patent [19]
Sato et al.

[11] Patent Number: 5,301,670
[45] Date of Patent: Apr. 12, 1994

[54] ULTRASONIC DIAGNOSIS APPARATUS

[75] Inventors: Takeshi Sato; Nobuo Yamazaki, both of Tochigi, Japan

[73] Assignee: Kabushiki Kaisha Toshiba, Kawasaki, Japan

[21] Appl. No.: 870,595

[22] Filed: Apr. 17, 1992

[30] Foreign Application Priority Data

Apr. 17, 1991 [JP] Japan .................................. 3-85232

[51] Int. Cl.$^5$ .............................................. A61B 8/00
[52] U.S. Cl. ........................... 128/660.05; 128/661.09
[58] Field of Search .......... 128/660.05, 661.07–661.10

[56] References Cited

U.S. PATENT DOCUMENTS

| | | | |
|---|---|---|---|
| 4,991,589 | 2/1991 | Hongo et al. | 128/661.09 |
| 5,014,710 | 5/1991 | Maslak et al. | 128/661.09 X |
| 5,083,567 | 1/1992 | Uchibori | 128/661.09 |
| 5,144,954 | 9/1992 | Satake | 128/661.09 |

Primary Examiner—Francis Jaworski
Attorney, Agent, or Firm—Oblon, Spivak, McClelland, Maier & Neustadt

[57] ABSTRACT

The present invention relates to an ultrasonic diagnosis apparatus for radiating ultrasonic waves in a cross section of a subject by color Doppler scan, detecting the intensity of reflected echo, and brightness-modulating the intensity of the reflected echo, thereby obtaining a tomogram of the subject, and also for detecting a frequency-deviation (Doppler shift) of the reflected echo and detecting the direction and flow velocity of a blood flow in the subject, thereby displaying the blood flow two-dimensionally by coloring the blood flow portion in the tomogram in accordance with the detected flow velocity and direction. The apparatus of the present invention has a control means for controlling the scan-timings for B-mode scanning and CFM scanning independently, and thus, the frame rate for B-mode scanning and that for CFM scanning are controlled independently. The B-mode scanning frame rate can be controlled to be higher than CFM scanning frame rate. Therefore, the realtime following ability for displaying B-mode image is improved compared to the conventional color Doppler scan.

12 Claims, 17 Drawing Sheets

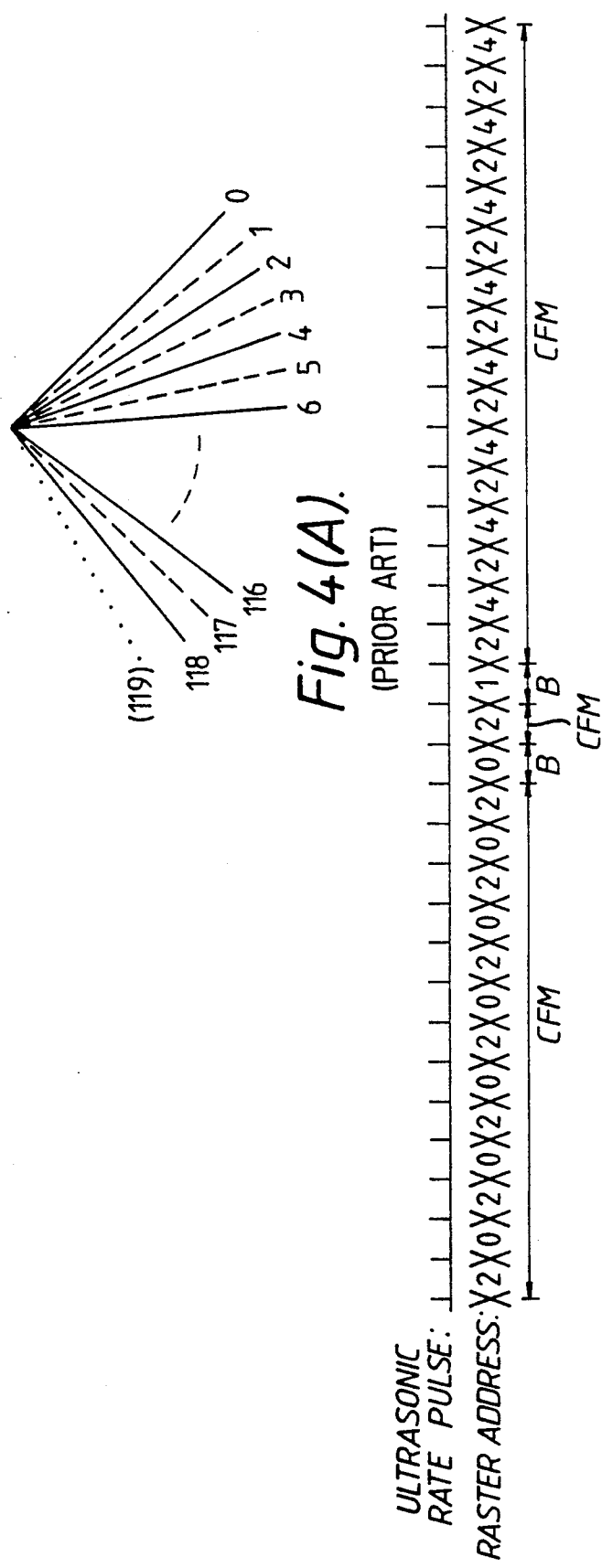
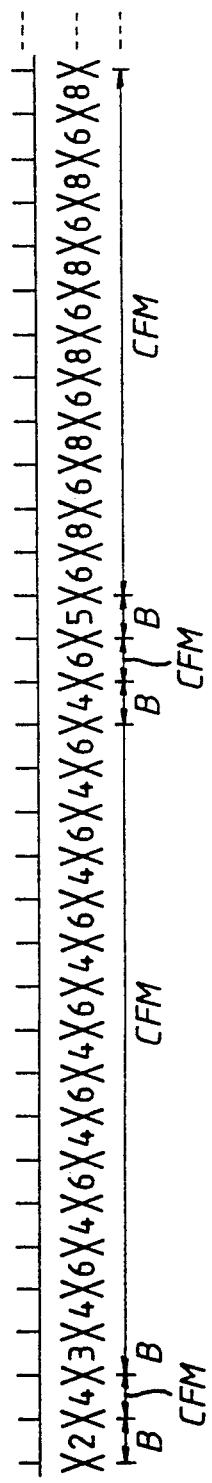
Fig. 4(A). (PRIOR ART)
Fig. 4(B). (PRIOR ART)

ULTRASONIC DIAGNOSIS APPARATUS

BACKGROUND OF THE INVENTION

Field of the Invention

The present invention relates to an ultrasonic diagnosis apparatus for radiating ultrasonic waves in a cross section of a subject by color Doppler scan, detecting the intensity of the reflected echo, and brightness-modulating the intensity of the reflected echo, thereby obtaining a tomogram of the subject, and also for detecting a frequency-deviation (Doppler shift) of the reflected echo and detecting the direction and flow velocity of a blood flow in the subject, thereby displaying the blood flow two-dimensionally by coloring the blood flow portion in the tomogram in accordance with the detected flow velocity and direction.

Description of the Related Art

This type of ultrasonic diagnosis apparatus is known as a color Doppler flow mapping apparatus, and in particular as a BDF apparatus, since it relates to blood flow imaging in a tomogram image (B-mode) display. A blood flow which approaches an ultrasonic probe is colored in red, a blood flow which moves away from the probe is colored in blue, and a turbulent flow is colored in green. The velocity of the blood flow is represented by brightness.

The BDF apparatus will now be described in brief. An ultrasonic Doppler method utilizes an ultrasonic Doppler shift wherein, when ultrasonic waves are reflected by a moving body, the frequency of the reflected waves shifts from a transmission frequency in proportion to the velocity of the object. Specifically, ultrasonic waves are radiated to a subject and the radiation direction is scanned in order to obtain a tomogram. In this case, ultrasonic pulses are transmitted repeatedly in respective directions in which ultrasonic waves are radiated, and a Doppler shift frequency is detected based on the phase variation of the reflected echoes. Thus, the data representing the movement of the moving body at a depth, at which the echo is reflected, is acquired. According to the ultrasonic Doppler method, it is possible to know the direction of the blood flow at a location in the subject and the condition of the blood flow (e.g. turbulent flow or regular flow).

In order to obtain blood flow data from an ultrasonic reflected echo signal, an ultrasonic probe is driven to repeatedly radiate ultrasonic waves in a raster direction for a number of times, and the received signal is detected by an orthogonal phase detecting circuit, thereby obtaining a Doppler shift signal on the basis of blood flow. Since a color Doppler image is obtained in real time, the Doppler shift signal is frequency-analyzed by a frequency analyzing circuit to find an average value of the Doppler shift, an average power of the Doppler shift, etc. A blood flow velocity color flow mapping (CFM) image is obtained by an auto-correlation circuit, etc., built in to the frequency analyzing circuit, and the blood flow velocity color flow mapping (CFM) image and a B-mode image are written in a digital scan converter (DSC). These images are read out from the digital scan converter (DSC) and the two-dimensional blood flow velocity CFM image is displayed on the B-mode image display on a TV monitor. Recently, this apparatus has been used to diagnose not only the heart but also those parts in which blood flow velocity is low, for example, blood vessels in the abdomen or peripheral blood vessels.

In the conventional color Doppler scan, the CFM scanning frame rate is equal to the B-mode scanning frame rate. FIGS. 1(A) and 1(B) show a first example of a conventional color Doppler scanning pattern. FIG. 1(A) shows 120 rasters, addressed 0th to 119th. For a B-mode scan, ultrasonic pulses are transmitted and ultrasonic data are received only 1 time for each raster. For a CFM scan, ultrasonic pulses are transmitted and ultrasonic data are received 16 times for each raster. In FIG. 1(B), the 0th raster is scanned 1 time by B-mode scan, and then the 0th raster is scanned continuously 16 times by CFM scan. Next, the 1st raster is scanned 1 time by B-mode scan, and then the 1st raster is scanned continuously 16 times by CFM scan. Then, in the same manner, the 2nd to 119th rasters are continuously scanned by B-mode scan and CFM scan. Thus, 1 frame of data for displaying a CFM image and a B-mode image is acquired. If the ultrasonic pulse repetition frequency (PRF) for transmitting ultrasonic pulse is 5 KHz, this first example's scanning frame rate FR1 is calculated as follows.

$$FR1 = (5 \times 10^3) / (120 \times 1 + 120 \times 16) = 2.45 \text{ (frames / 1 second)}$$

This scanning frame rate FR1 is for B-mode scan and CFM scan, and then the B-mode display frame rate is equal to the CFM display frame rate.

FIGS. 2(A) and 2(B) show a second example of a conventional color Doppler scanning pattern. FIG. 2(A) shows 120 rasters, addressed 0th to 118th and 1 dummy raster. For a B-mode scan, ultrasonic data are transmitted and received only 1 time for each raster. For a CFM scan, ultrasonic data are transmitted and received 16 times for each alternate raster (a total 60 rasters) for collecting CFM image data. In FIG. 2(B), first, the 0th raster is scanned 1 time by B-mode scan, and then the 0th raster is scanned continuously 16 times by CFM scan. Next, the 1st and 2nd rasters are scanned 1 time for each by the B-mode scan, and then the 2nd raster is scanned continuously 16 times by the CFM scan. Then, the 3rd to 119th rasters are scanned by B-mode scan and CFM scan as described above. Thus, 1 frame of data for displaying CFM image and B-mode image is acquired. If the PRF for transmitting the ultrasonic pulse is 5 KHz, this second example's scanning frame rate FR2 is calculated as follows.

$$FR2 = (5 \times 10^3) / (120 \times 1 + 60 \times 16) = 4.63 \text{ (frames / 1 second)}$$

This scanning frame rate FR2 is for B-mode scan and CFM scan, and then the B-mode display frame rate is equal to the CFM display frame rate.

FIGS. 3(A) and 3(B) show a third example of a conventional color Doppler scanning pattern, related to U.S. Pat. No 4,993,417. FIG. 3(A) shows 120 rasters, addressed 0th to 118th and 1 dummy raster. For a B-mode scan, each raster transmits and receives ultrasonic data only 1 time for collecting the B-mode image data. For a CFM scan, each alternate raster (a total 60 rasters) transmits and receives ultrasonic data 16 times for collecting the CFM image data. In FIG. 3(B), the 0th and 2nd rasters are alternately scanned 16 times for each by CFM scan. Next, the 0th to 3rd rasters are scanned 1 time for each by B-mode scan. Then, as described above, the 4th to the 119th rasters are scanned by B-mode scan and CFM scan. Thus, 1 frame data for displaying a CFM image and a B-mode image is acquired. If PRF for transmitting ultrasonic pulse is 5 KHz, this third example's scanning frame rate FR3 is calculated as follows.

$$FR3 = (5 \times 10^3) / (120 \times 1 + 60 \times 16) = 4.63 \text{ (frames / 1 second)}$$

This scanning frame rate FR3 is for B-mode scan and CFM scan, and then the B-mode display frame rate is equal to the CFM display frame rate. This third examples' CFM scanning rate for each is 2 times longer than the second example's CFM scanning blood flow detected by the third examples' scanning pattern can be 50 percent slower than by the second examples' scanning pattern. Then, it is possible to observe slower velocity of blood flow by the third example than the second example.

FIGS. 4(A) and 4(B) show a fourth example of a conventional color Doppler scanning pattern, related to U.S. Pat. No. 4,993,417. FIG. 4(A) shows 120 rasters, addressed 0th to 118th and 1 dummy raster. For a B-mode scan, ultrasonic data are transmitted and received only 1 time for each raster. For a CFM scan, ultrasonic data are transmitted and received 16 times for each alternate raster (total 60 rasters) for collecting CFM image data. In FIG. 4(B), first, the 2nd and 0th rasters are alternately scanned 6 times for each by CFM scan. Next, the 2nd raster is scanned 1 time by CFM scan, then the 0th raster is scanned 1 time by B-mode scan, then the 2nd raster is scanned 1 time by CFM scan, then the 1st raster is scanned 1 time by B-mode scan. Next, the 2nd and 4th rasters are alternately scanned 8 times for each by CFM scan. Then, as described above, all rasters are scanned by B-mode scan and CFM scan in the same pattern. Thus, 1 frame of data for displaying a CFM image and a B-mode image is acquired. If the PRF for transmitting the ultrasonic pulse is 5 KHz, this second example's scanning frame rate FR4 is calculated as follows.

$$FR4 = (5 \times 10^3) / (120 \times 1 + 60 \times 16) = 4.63 \text{ (frames / 1 second)}$$

This scanning frame rate FR4 is for the B-mode scan and the CFM scan, and then the B-mode display frame rate is equal to the CFM display frame rate. This fourth example's scanning pattern is able to collect and output B-mode image data and CFM image data at same the intervals for each raster.

These conventional BDF apparatuses, however, have the following problem. As stated above, the B-mode scanning frame rate is equal to the CFM scanning frame rate, and the CFM scan needs a longer time to collect the image data for each raster than the B-mode scan, therefore the B-mode frame rate is depended on the CFM frame rate. For example, when the ultrasonic probe is moved on a subject during scanning by color Doppler scan, the amount of change caused in the B-mode image as a result of time direction changes and space direction changes is bigger than the amount of change in the CFM image. This is because the resolutional ability of the B-mode image is far higher than that of the CFM image. Thus, the ability of the B-mode image display depends on the B-mode frame rate. In other words, the B-mode, frame rate generated by a color Doppler scan is dependent on the CFM frame rate. Therefore, the B-mode frame rate generated by a color Doppler scan is too slow compared to the B-mode frame rate generated by a B-mode scan, and it is thus more difficult to diagnose from a B-mode image by the color Doppler scan than from a B-mode image by the B-mode scan.

SUMMARY OF THE INVENTION

It is an object of the present invention to provide an ultrasonic diagnosis apparatus capable of improving the ability to use images developed by a B-mode image display using a color Doppler scan.

In order to achieve the above object, according to the present invention, there is provided an ultrasonic diagnosis apparatus for displaying an ultrasonic image, which image is obtained by data from a plurality of rasters scanned by an ultrasonic imaging transducer, comprising:

transducer means;

B-mode scanning means for scanning each raster by controlling the transducer means such that the transducer means transmits an ultrasonic pulse and receives a reflected echo from each raster;

CFM scanning means for scanning each raster by controlling the transducer means such that the transducer means transmits plural ultrasonic pulses and receives plural reflected echoes from each raster;

B-mode imaging means for calculating an intensity data from the reflected echo scanned by the B-mode scanning means for each raster, and for producing a tomogram image for a frame from the intensity data calculated in a plurality of rasters;

CFM imaging means for calculating a Doppler shift data from the reflected echoes scanned by the CFM scanning means for each raster, and for producing a color flow mapping image for a frame from the Doppler shift data calculated in a plurality of rasters;

display means for displaying the color flow mapping image on the tomogram image; and scan controlling means for independently controlling a first scanning frame rate used by the B-mode scanning means for scanning a frame and a second scanning frame rate used by the CFM scanning means for scanning a frame, wherein the first scanning frame rate used by the B-mode scanning means for scanning a frame is higher than the second scanning frame rate used by the CFM scanning means for scanning a frame.

According to the ultrasonic diagnosis apparatus of the present invention, the B-mode scanning frame rate may be controlled so that it is higher than the CFM scanning frame rate. Therefore, the realtime following ability for displaying B-mode image is improved from the conventional color Doppler scan.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and the detailed description of the preferred embodiment given below serves to explain the principles of the invention.

FIGS. 4(A) and 4(B) show the fourth example of a conventional color Doppler scanning pattern;

DETAILED DESCRIPTION OF THE PREFERRED EMBODIMENTS

An ultrasonic diagnosis apparatus according to an embodiment of the present invention will be described below with reference to the accompanying drawings.

Figure 5:
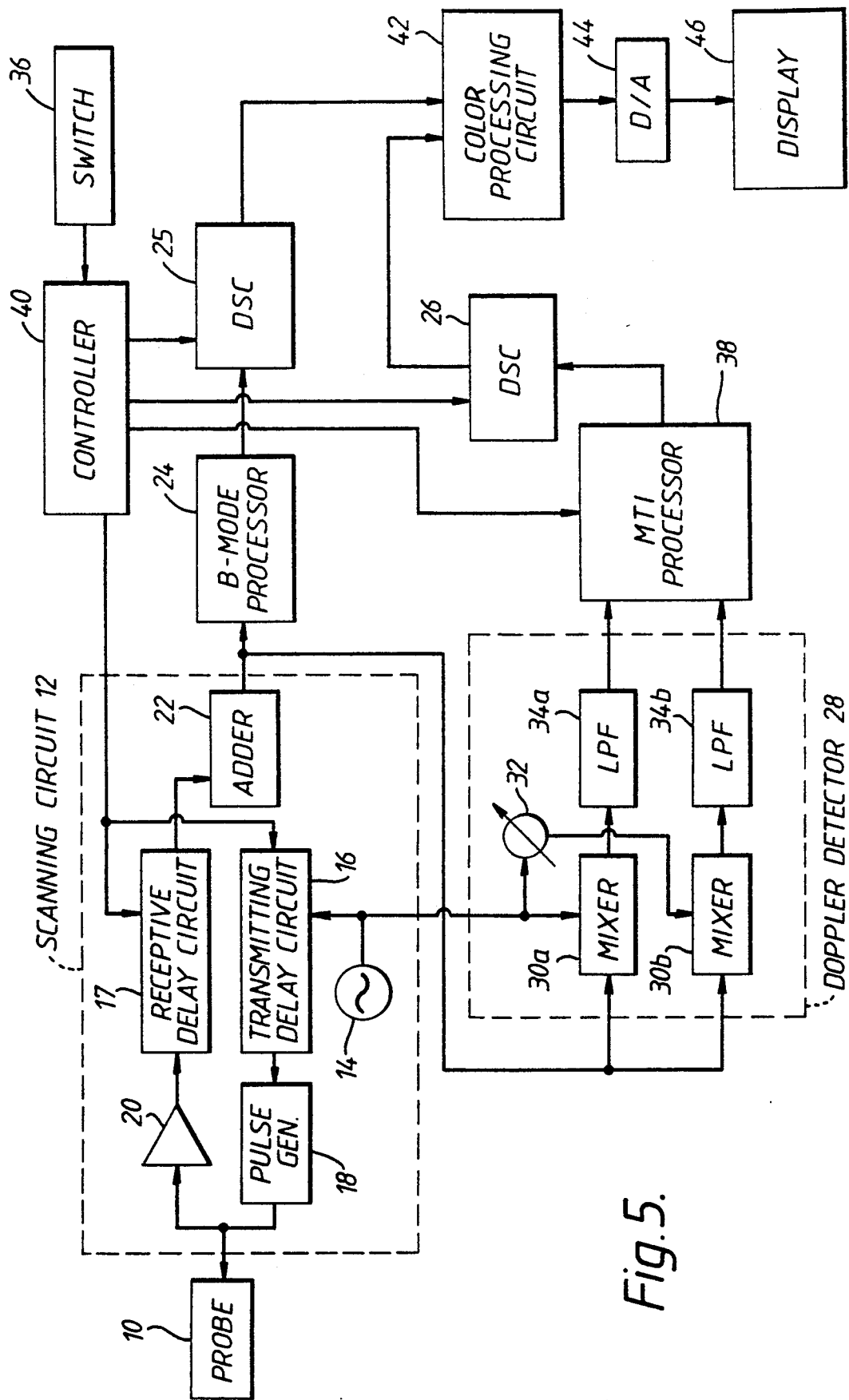
FIG. 5 is a block diagram showing an ultrasonic diagnosis apparatus according to the present invention.

In FIG. 5, a scanning circuit 12 is connected to an electronic sector scanning type ultrasonic probe 10. A probe 10 comprises a large number of piezoelectric transducers arrayed in a row. By varying the timing of voltages applied to the respective transducers, it is possible to cause ultrasonic beams to scan a sector or to focus the ultrasonic beams. The probe 10 need not be limited to the electronic sector scanning type and it may be of a linear scanning type or a mechanical scanning type.

In the scanning circuit 12, an output of an oscillator 14, which determines an oscillation frequency of the transducers, is applied to the probe 10 via a transmitting delay circuit 16 and a pulse generator 18. The pulse generator 18 periodically supplies the probe 10 with driving pulses. The inverse of the period is the repetition frequency (rate frequency) of the ultrasonic beams. By varying the delay times of the delay circuit 16, it becomes possible to vary the directions of the ultrasonic pulses transmitted to a subject from the probe 10. The delay times are controlled by control signals from a controller 40.

An output from the probe 10 is supplied to an adder 22 through a preamplifier 20 and a receptive delay circuit 17. The delay circuit 17 comprises a large number of delay lines having variable delay times. By varying the delay times of the respective delay lines, it becomes possible to vary the directions (raster directions) of the ultrasonic pulses received from the subject by the probe 10. The delay times are controlled by control signals from the controller 40. In order to detect an B-mode image (tomogram image), it is necessary to transmit and receive a ultrasonic pulse in the same raster direction. In order to detect a color flow mapping (CFM) image, it is necessary to transmit and receive ultrasonic pulses in the same raster direction for several times.

The controller 40, connected from an operation switch 36, controls scan-timings for B-mode scanning and CFM scanning independently, and thus the frame rate for B-mode scanning and for CFM scanning are controlled independently. Therefore, the controller 40, in this embodiment, can control the system so that the frame rate for B-mode scanning is higher than the frame rate for CFM scanning.

Figure 6:
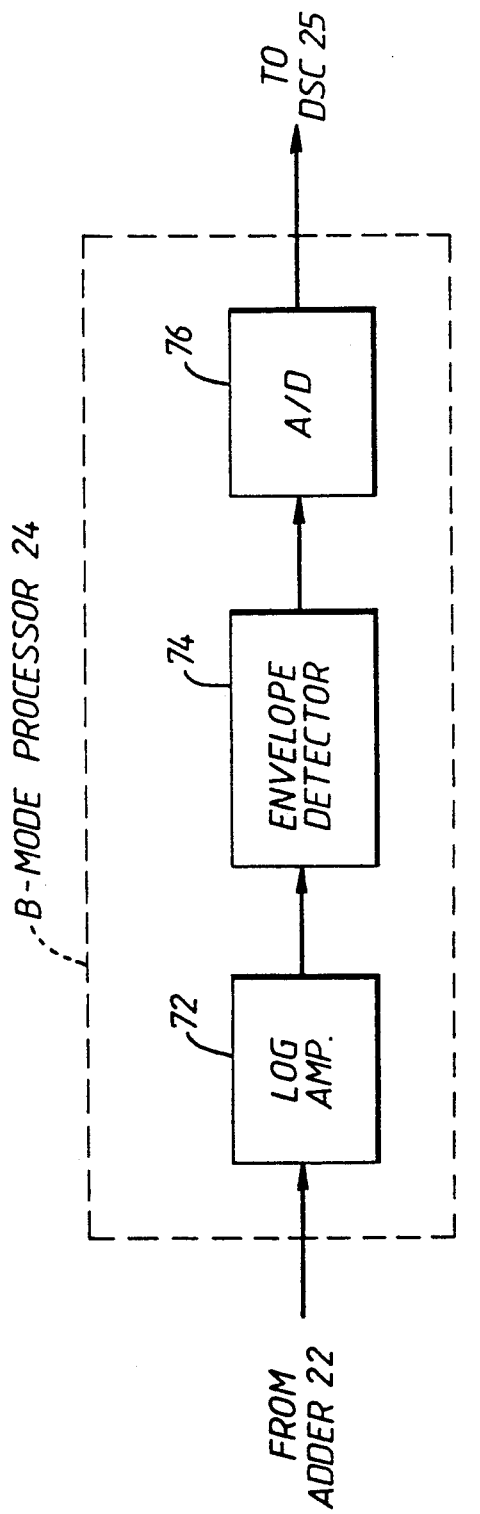
FIG. 6 is a block diagram showing in detail a B-mode processor according to the present invention.

An output, obtained by B-mode scan, from the adder 22 is input to a B-mode processor 24, and the intensity of the reflected ultrasonic echo in each raster direction is detected. The B-mode processor 24 has a structure as shown in FIG. 6, and comprises a logarithmic amplifier 72, an envelope detector 74 and A/D converter 76. The logarithmic amplifier 72 logarithmic-amplifies a received signal output from the adder 22, and the envelope detector 74 detects an envelope of the signal from the amplifier 72. An output from B-mode processor 24 is input to a first digital scan converter (DSC) 25 as brightness data of each raster, that is, B-mode image (tomogram) data. The raster of the ultrasonic probe 10 is changed in a sectional fashion, but the raster of a color monitor(display) 46 is lateral, as in a standard TV system. Thus, the DSC 25 alters the raster direction (scan direction) of the input image and outputs the resultant image.

An output, obtained by CFM scan, from the adder 22 and an output from the oscillator 14 are supplied to a Doppler detector 28. The Doppler detector 28 is a circuit for detecting the Doppler shift frequency by an orthogonal detection method. The Doppler detector 28 comprises mixers 30a and 30b, a 90° phase shifter 32, and low-pass filters (LPF) 34a and 34b. An output from the adder 22 is multiplied by an output from the oscillator 14 in the mixer 30a and the output from the adder 22 is multiplied by an output from the phase shifter 32 in the mixer 30b. Each of the mixers 30a and 30b outputs a signal containing a Doppler shift frequency component and a high-frequency component (double the transmission frequency). The LPFs 34a and 34b remove the high-frequency component and a sine component of the Doppler shift frequency. The Doppler shift frequency is then provided to two channels for the cosine and sine components, in order to detect the polarity of shift frequency.

Figure 7:
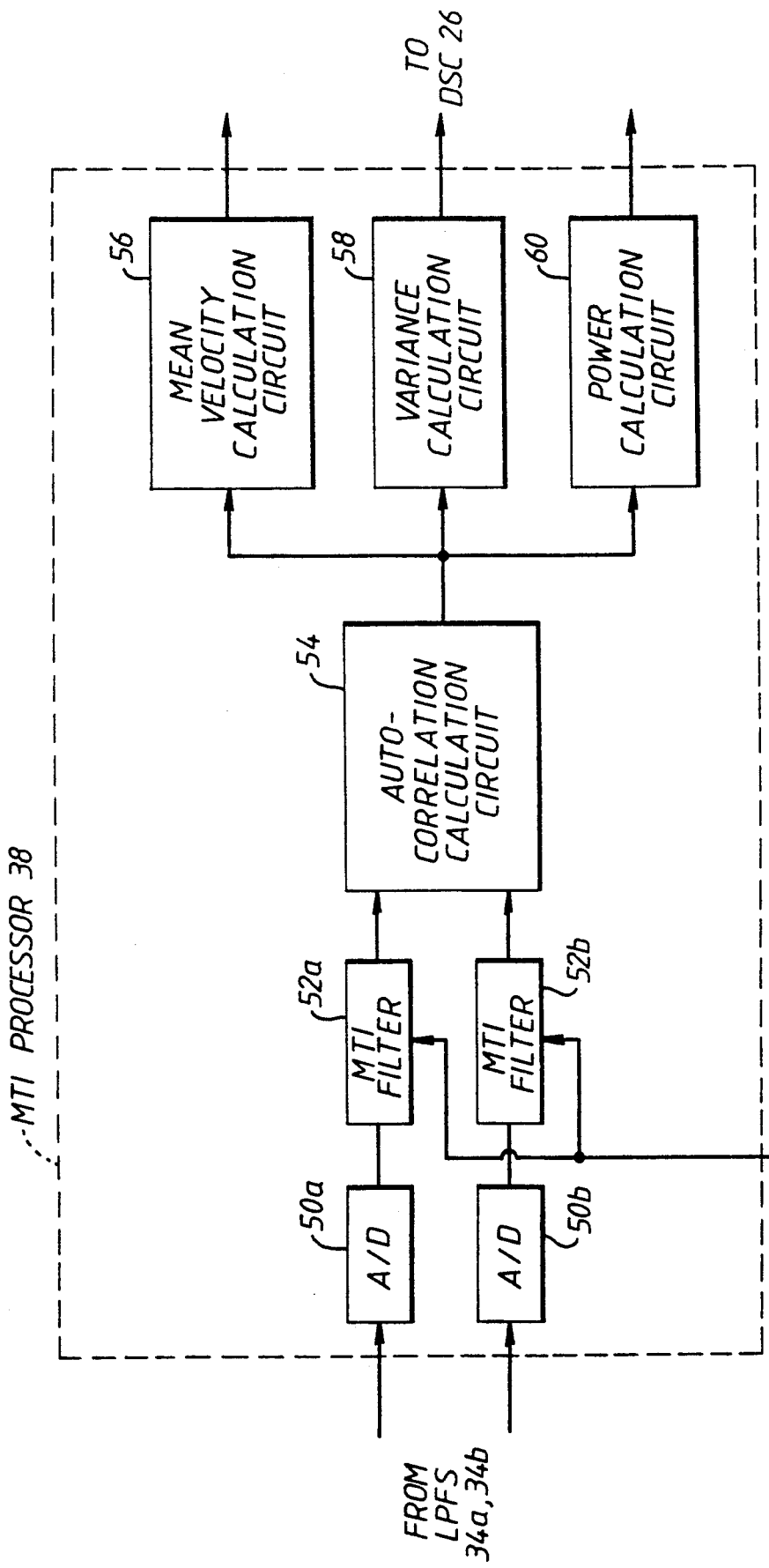
FIG. 7 is a block diagram showing in detail a MTI processor according to the present invention.

The output from the Doppler detector 28 is supplied to an MTI (Moving Target Indicator) processor 38 for color flow mapping (CFM) image FIG. 7 is a block diagram showing the MTI processor 38 in detail. The outputs from the LPFs 34a and 34b are supplied to an auto-correlation calculation circuit 54 through A/D converters 50a and 50b and MTI filters 52a and 52b.

The auto-correlation calculation circuit 54 is employed to perform, in real time, frequency analysis of many points distributed two-dimensionally. Compared to an FFT (Fast Fourier Transform) process, the number of arithmetic operations decreases. The output from the auto-correlation calculation circuit 54 is supplied to a mean velocity calculation circuit 56, a variance calculation circuit 58, and a power calculation circuit 60. The outputs from the calculation circuits 56, 58 and 60 are supplied to a second DSC 26. Thus, the MTI processor 38 can acquire blood flow data at each point on a tomogram obtained by the B-mode processor 24.

The MTI filters 52a and 52b function to remove unnecessary reflected echoes (clutter component) from a stationary reflector (blood vessel wall, heart wall, etc.). The filters 52a and 52b comprise digital filters having low-pass characteristics. Specifically, the MTI filters 52a and 52b detect the movement of blood flow on the basis of the phase variation, with respect to the same pixel, between the echo signals obtained from several different ultrasonic radiations in the same raster direction, and remove the clutter component. Alternatively, the MTI filters may have an analog construction and be composed of delay lines and subtracters for subtracting, from the reflected signals, the reflected signals obtained after a predetermined time period, thereby removing the clutter component.

A mean value v of the Doppler shift frequency, a variance $\sigma^2$, and total power TP respectively output from the mean velocity calculation circuit 56, variance calculation circuit 58, and power calculation circuit 60 are supplied to the DSC 26 for blood flow data. The total power TP is proportional to the intensity scattered echo from the blood flow, but an echo from a moving body having a frequency not higher than the cut-off frequency of the MTI filters 52a and 52b is removed. Like the DSC 25, the DSC 26 alters the scanning direction of the input blood flow data and outputs the resultant data, and, where necessary, performs frame interpolation. The details of the DSC 26 will be described later.

Control signals from the controller 40 are also supplied to the MTI processor 38, DSC 25 and DSC 26. The monochromatic tomogram and blood flow data, which are output from the DSCs 25 and 26, are supplied to a color processing circuit 42. As in the conventional art, the blood flow portion in the tomogram is colored such that the direction of the blood flow towards the probe is expressed in red, the direction away from the probe is in blue, the mean velocity is in brightness, and the velocity distribution is expressed by hues (mixed with green), thereby producing a color Doppler image. The output from the color processing circuit 42 is supplied to display 46 through a D/A converter 44. Though not shown, the output from the D/A converter 44 may be supplied to a recording section such as a VTR, as well.

Figure 8:
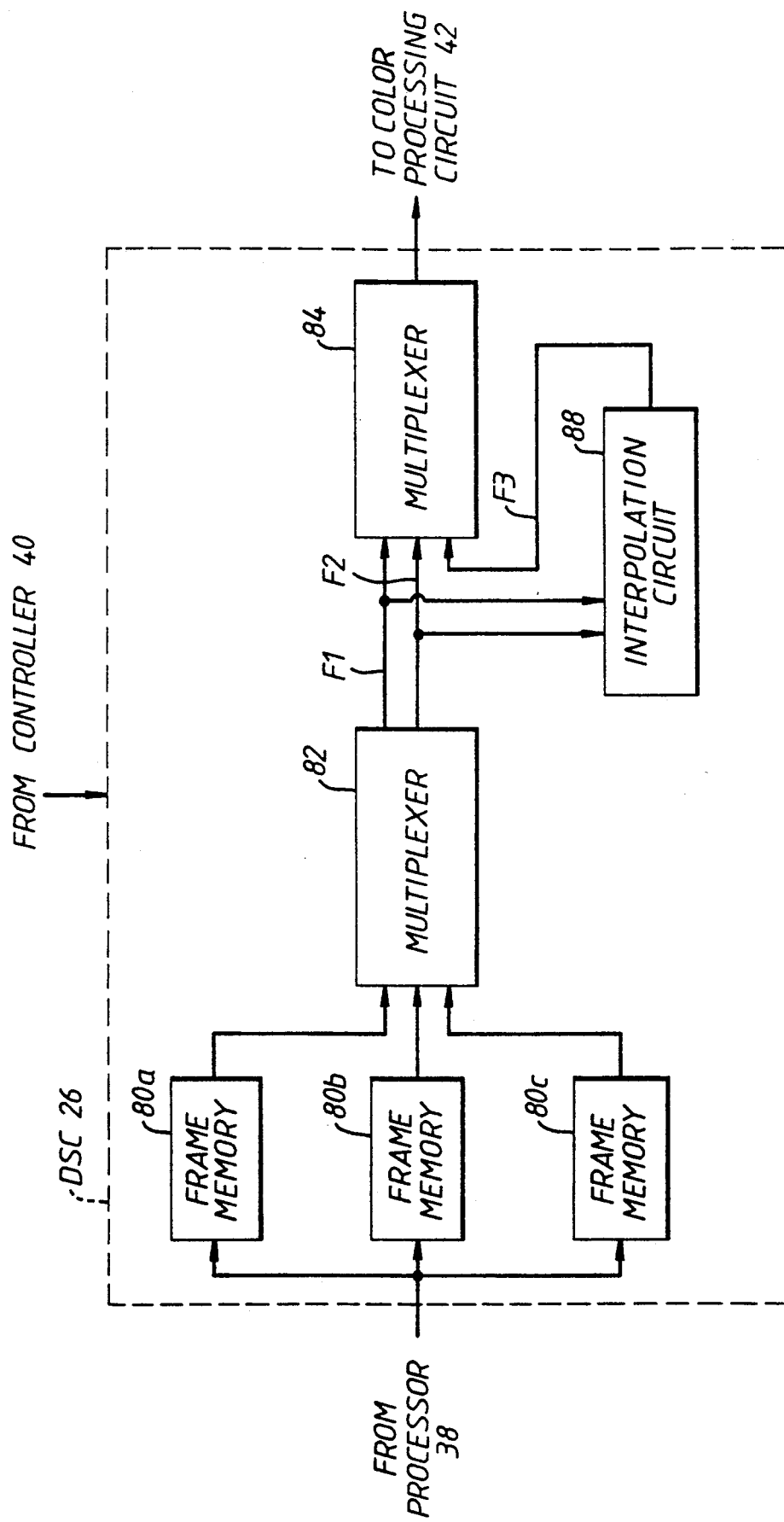
FIG. 8 is a block diagram showing in detail a blood flow data DSC according to the present invention.

FIG. 8 is a block diagram showing in detail the second DSC 26 for blood flow data. The DSC 26 comprises three frame memories 80a, 80b, and 80c, multiplexers (MUX) 82 and 84 functioning as control means, and an interpolation circuit 88 functioning as interpolation means. The first DSC 25 for tomogram data has the same construction as the second DSC 26, except that the interpolation circuit 88 is omitted.

The three frame memories 80a to 80c are controlled by control signals from the controller 40, and store blood flow data supplied successively in units of a frame. The blood flow data of each frame is successively written in the frame memories 80a to 80c. While one frame memory is set in the write mode, the other two frame memories are set in the read mode. Thus, the blood flow data of the same frame is read from each frame memory for a two-frame period. The outputs from the frame memories 80a to 80c are supplied to the three-inputs/two-outputs multiplexer 82. The multiplexer 82 delivers the outputs of the frame memories set in the read mode as first and second output signals F1 and F2. Thus, the output signals F1 and F2 of the multiplexer 82 are, respectively, the data of the second frame prior to the presently written frame, and the data of the first frame prior to the present frame, i.e., the prior frame. For example, in the period in which the third-frame data is written in the frame memory 80c, the first frame and the second frame data read out from the frame memories 80a and 80b, and the read-out data are output from the multiplexer 82 as first and second signals F1 and F2.

Figure 9:
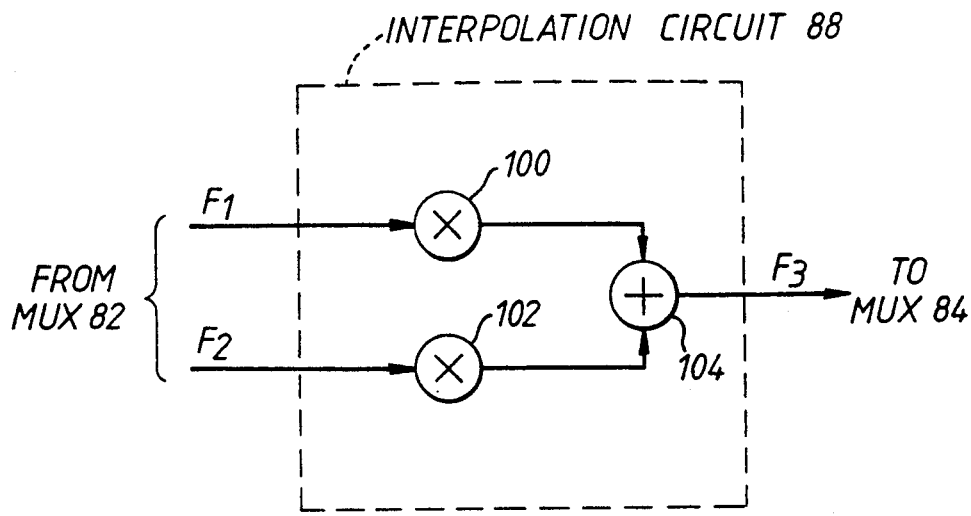
FIG. 9 is a block diagram showing in detail an interpolation circuit according to the present invention.

The two outputs from the multiplexer 82 are supplied to a three-inputs/one-output multiplexer 84 and an interpolation circuit 88. The output from the interpolation circuit 88 is supplied to a third input terminal of the multiplexer 84. The interpolation circuit 88 interpolates the flow velocity data of an intermediate frame based on the flow velocity data F1 and F2 of the second and first frames prior to the present frame. The interpolation circuit 88 has a structure, for example, as shown in FIG. 9. The flow velocity data F1 and F2 are multiplied by a coefficient by multipliers 100 and 102, and the multiplied values are added by an adder 104. The added result F3 is supplied to the multiplexer 84 as interpolation flow velocity data. Then, several number of interpolated imaging frames between the two scanned CFM imaging frames are obtained by changing the coefficient. By frame interpolating the CFM image, the display frame rate thereof can be several times. In this embodiment, the number of interpolated CFM imaging frames between two scanned CFM imaging frames is determined by comparing the scanning frame rate for B-mode scanning with the CFM scanning rate.

Next, the scanning patterns of the apparatus of the present invention will be described.

Figure 10A:
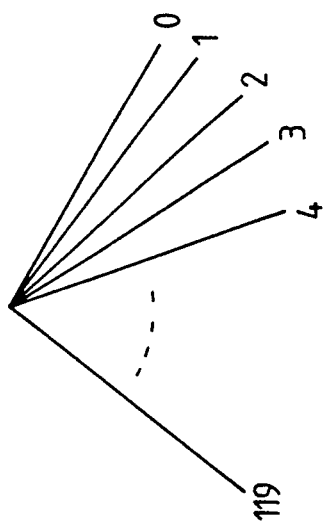
FIGS. 10(A) and 10(B) show the first example of the invention's color Doppler scanning pattern.
Figure 10B:
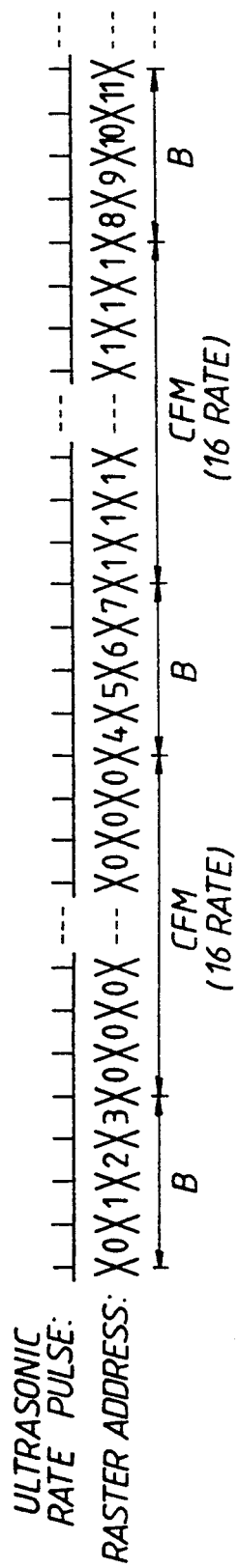

FIGS. 10(A) and 10(B) show a first example of a color Doppler scanning pattern of this invention. FIG. 10(A) shows 120 rasters, addressed 0th to 119th. For a B-mode scan, ultrasonic data are only transmitted and received 1 time for each raster. For a CFM scan, ultrasonic data are transmitted and received 16 times for each raster. In FIG. 10(B), the 0th to 3rd rasters are each scanned 1 time by B-mode scan, and then the 0th raster is scanned continuously 16 times by CFM scan. Next, the 4th to 7th rasters are each scanned 1 time by B-mode scan, and then the 1st raster is scanned continuously 16 times by CFM scan. Then alternately, as described above, 4 rasters are scanned by B-mode scan and 1 raster is scanned by CFM scan. Therefore, 30 rasters are scanned by CFM scan while 120 rasters (1 frame) are scanned by B-mode scan, and 4 frames (120×4 rasters) are scanned by B-mode scan while 1 frame is scanned by CFM scan. Thus, one frame of data for displaying a CFM image and a B-mode image is acquired. If the PRF for transmitting the ultrasonic pulse is 5 KHz, the B-mode scanning frame rate BFR1 and the CFM scanning frame rate CFR1 in this first embodiment are calculated as follows.

$$BFR1=(5\times10^3)/(120\times1+30\times16)=8.33 \text{ (frames / 1 second)}$$

$$CFR1=(5\times10^3)/(120\times16+120\times4)=2.08 \text{ (frames / 1 second)}$$

Figure 1A:
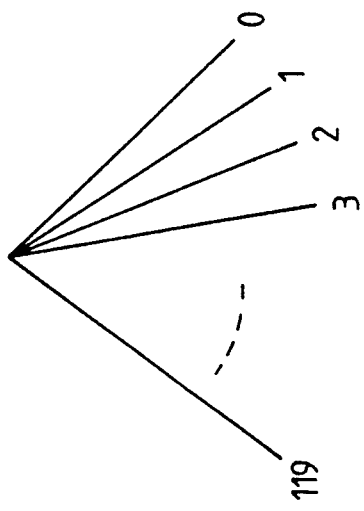
FIGS. 1(A) and 1(B) show the first example of a conventional color Doppler scanning pattern.
Figure 1B:
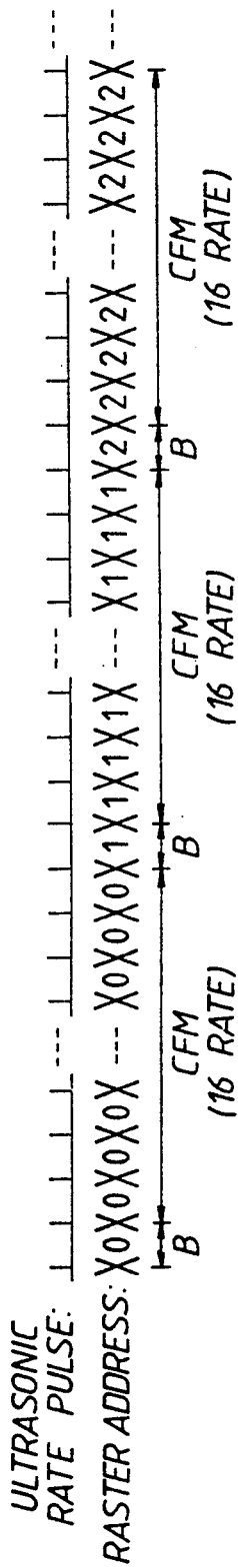
Figure 11:
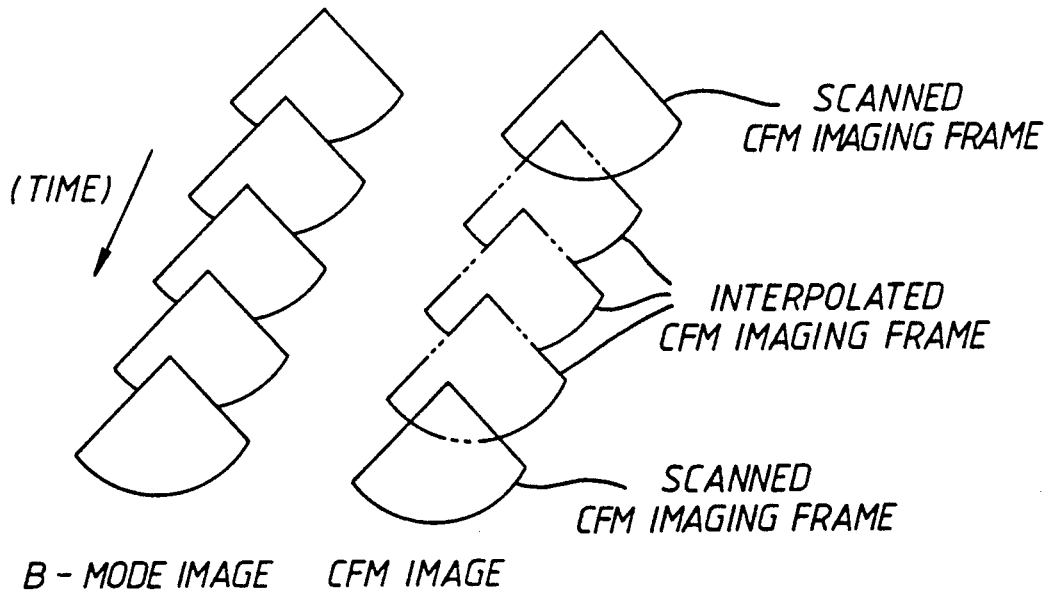
FIG. 11 shows a comparison between B-mode scanning frames and CFM scanning frames for the first example of the invention's color Doppler scan.

This means that the B-mode scanning frame rate BFR1 is about 4 times (=8.33/2.08) higher than the CFM scanning frame rate CFR1, and the BFR1 is about 3.4 times higher than the B-mode frame rate FR1 (=2.45) of the conventional color Doppler scan and the CFR1 is about equal to the CFM frame rate FR1 of the conventional color Doppler scan in FIG. 1. Therefore, the realtime following ability for displaying B-mode image is 3.4 times improved from the conventional color Doppler scan. Then, three interpolated CFM imaging frames, produced by DSC 26, are inserted between two scanned CFM imaging frames as shown in FIG. 11, and the CFM images are displayed on the scanned B-mode images on display 46.

Figure 12A:
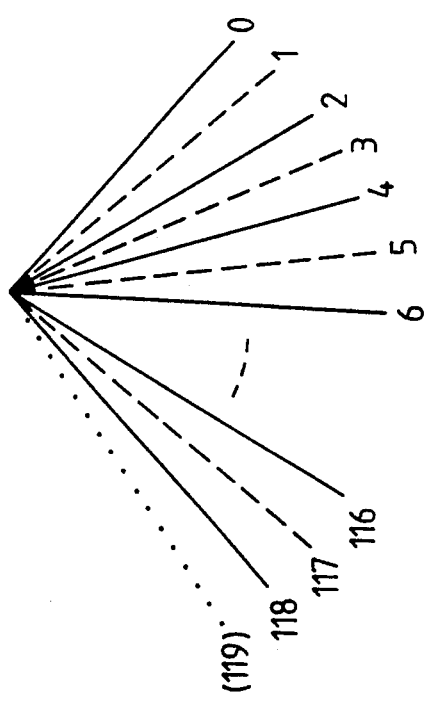
FIGS. 12(A) and 12(B) show the second example of the invention's color Doppler scanning pattern.
Figure 12B:
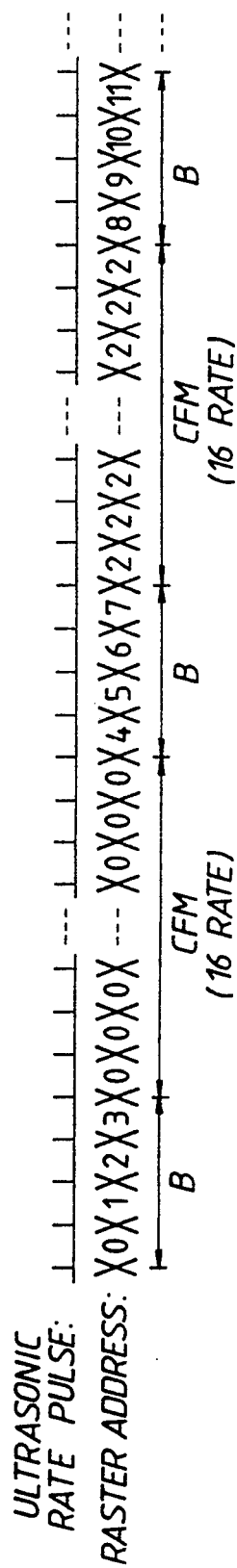

FIGS. 12(A) and 12(B) show a second example of a color Doppler scanning pattern according to the invention. FIG. 12(A) shows 120 rasters, addressed 0th to 118th and 1 dummy raster. For a B-mode scan, ultrasonic data are transmitted and received only 1 time for each raster for collecting B-mode image data. For a CFM scan, ultrasonic data are transmitted and received 16 times for each alternate raster (total 60 rasters) for collecting CFM image data. In FIG. 12(B), first, the 0th to 3rd rasters are each scanned 1 time by B-mode scan, and then the 0th raster is scanned continuously 16 times by CFM scan. Next, the 4th and 7th rasters are each scanned 1 time by B-mode scan, and then the 2nd raster is scanned continuously 16 times by CFM scan. Then alternately, as described above, 4 rasters are scanned by B-mode scan and 1 raster is scanned by CFM scan. Therefore, 30 rasters are scanned by CFM scan while 120 rasters (1 frame) are scanned by B-mode scan, and 2 frames (120×2 rasters) are scanned by B-mode scan while 1 frame (60 rasters) are scanned by CFM scan. Thus, one frame of data for displaying a CFM image and a B-mode image is acquired. If the PRF for transmitting the ultrasonic pulse is 5 KHz, the B-mode scanning frame rate BFR2 and the CFM scanning frame rate CFR2 in this second embodiment are calculated as follows.

$$BFR2=(5\times10^3)/(120\times1+30\times16)=8.33 \text{ (frames / 1 second)}$$

$$CFR2=(5\times10^3)/(60\times16+120\times2)=4.17 \text{ (frames / 1 second)}$$

Figure 2A:
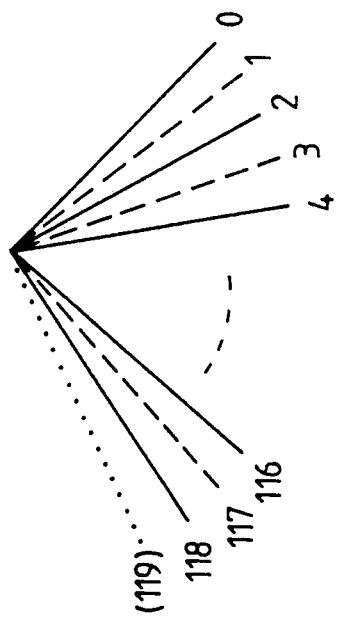
FIGS. 2(A) and 2(B) show the second example of a conventional color Doppler scanning pattern.
Figure 2B:
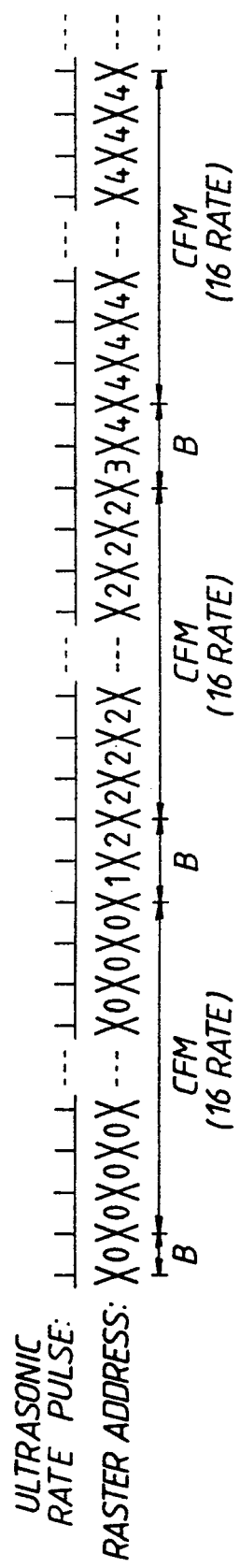

This means that the B-mode scanning frame rate BFR2 is about 2 times (=8.33/4.17) higher than the CFM scanning frame rate CFR2, and the BFR2 is about 1.8 times higher than the B-mode frame rate FR2 (=4.63) of the conventional color Doppler scan and the CFR2 is about 0.9 times higher than the CFM frame rate FR2 of the conventional color Doppler scan in FIG. 2. Therefore, the realtime following ability for displaying B-mode image is 1.8 times improved from the conventional color Doppler scan. One interpolated CFM imaging frame, produced by DSC 26, is inserted between two scanned CFM imaging frames, and the CFM images are displayed on the scanned B-mode images on display 46.

Figure 13A:
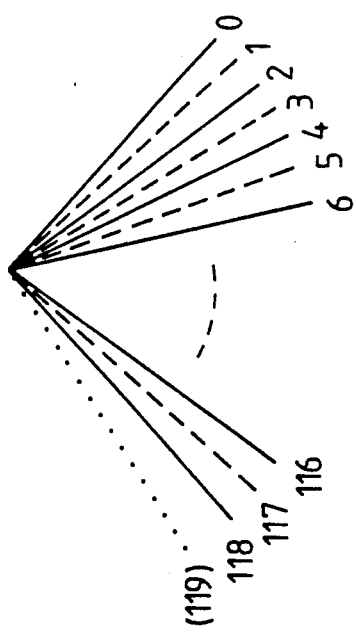
FIGS. 13(A) and 13(B) show the third example of the invention's color Doppler scanning pattern.
Figure 13B:
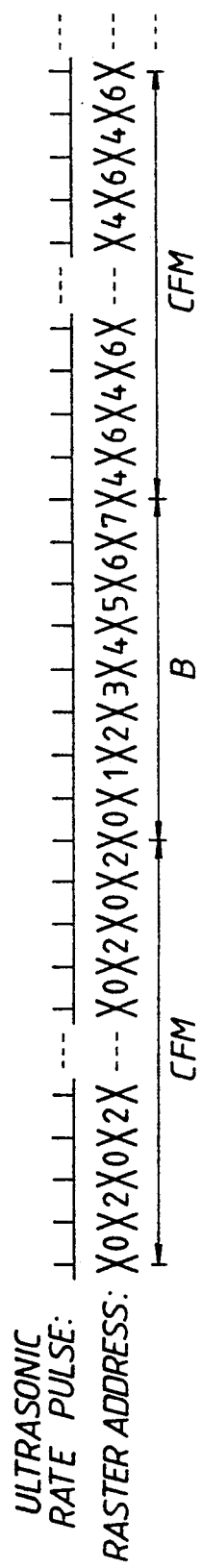

FIGS. 13(A) and 13(B) show a third example of a color Doppler scanning pattern according to this invention. FIG. 13(A) shows 120 rasters, addressed 0th to 118th and 1 dummy raster. For a B-mode scan, ultrasonic data are transmitted and received 1 time for each raster for collecting B-mode image data, and for a CFM scan, ultrasonic data are transmitted and received 16 times for alternate raster (total 60 rasters) for collecting CFM image data. In FIG. 13(B), the 0th and 2nd rasters are alternately scanned 16 times for each by CFM scan, and then the 0th to 7th rasters are scanned 1 time for each by B-mode scan. Next, the 4th and 6th rasters are alternately scanned 16 times for each by CFM scan, and then the 8th to 15th rasters are scanned 1 time for each by B-mode scan. Then alternately, as described above, alternate rasters are scanned by CFM scan and 8 rasters are scanned by B-mode scan as shown in FIG. 13(B). Therefore, 30 rasters are scanned by CFM scan while 120 rasters (1 frame) are scanned by B-mode scan, and 2 frames (120 2 rasters) are scanned by B-mode scan while 1 frame (60 rasters) is scanned by CFM scan.

Figure 14:
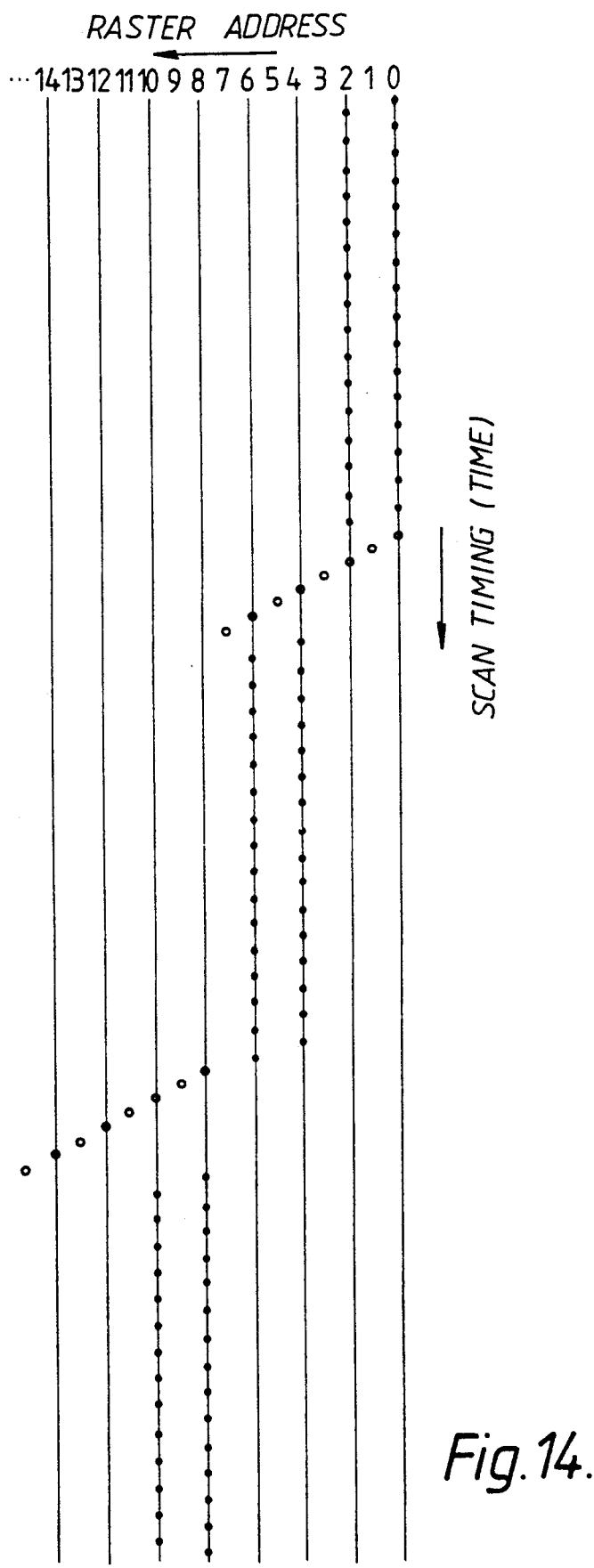
FIG. 14 shows the relationship between raster addresses and scanning timing for the third example of the invention's color Doppler scan.

This scanning method is called interleave scan, and a chart of this scan-timing and raster addresses are shown in FIG. 14. In FIG. 14, a black dot (•) shows a timing for CFM scanning, and a white dot (○) shows a timing for B-mode scanning. In this interleave scan, the CFM scanning rate for each raster is two times lower than the rate of the scanning method shown in FIG. 12, therefore it can detect two times slower velocity of blood flow than the method illustrated by the scanning method illustrated in FIG. 12. If n (n >=2) rasters are alternately scanned 16 times each by the CFM scan, it can detect n times slower velocity of blood flow than can be detected by the scanning method of FIG. 13.

Thus, one frame data for displaying a CFM image and a B-mode image is acquired. If the PRF for transmitting the ultrasonic pulse is 5 KHz, the B-mode scanning frame rate BFR3 and the CFM scanning frame rate CFR3 in this third embodiment are calculated as follows.

$$BFR3=(5\times10^3)/(120\times1+30\times16)=8.33 \text{ (frames / 1 second)}$$

$$CFR3=(5\times10^3)/(60\times16+120\times2)=4.17 \text{ (frames / 1 second)}$$

Figure 3A:
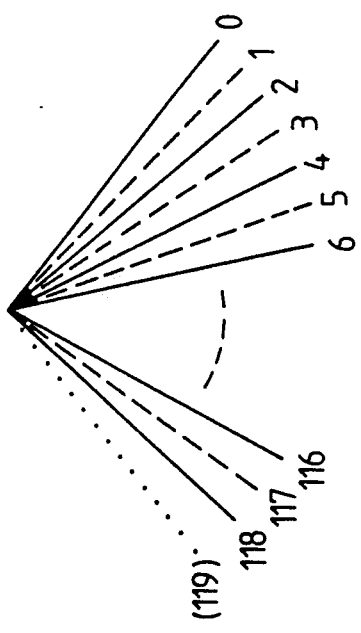
FIGS. 3(A) and 3(B) show the third example of a conventional color Doppler scanning pattern.
Figure 3B:
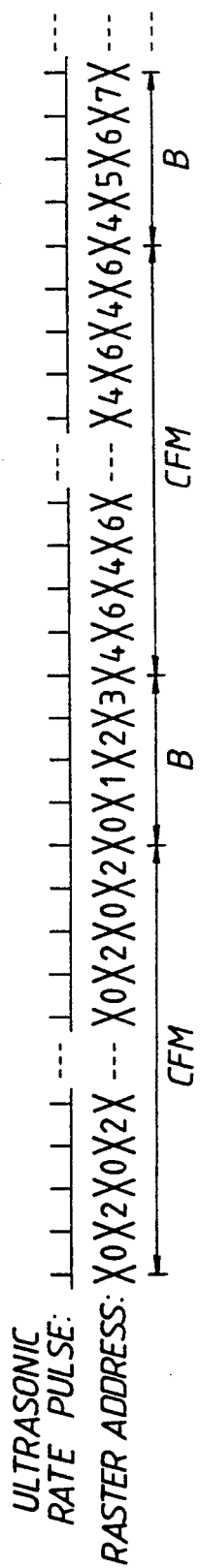

This means that the B-mode scanning frame rate BFR3 is about 2 times (=8.33/4.17) higher than the CFM scanning frame rate CFR3, and the BFR3 is about 1.8 times higher than the B-mode frame rate FR2 (=4.63) of the conventional color Doppler scan and the CFR3 is about 0.9 times higher than the CFM frame rate FR3 of the conventional color Doppler scan in FIG. 3. Therefore, the realtime following ability for displaying B-mode image is 1.8 times improved from the conventional color Doppler scan. One interpolated CFM imaging frame, produced by DSC 26, is inserted between two scanned CFM imaging frames, and the CFM images are displayed on the scanned B-mode images on display 46.

Figures 15A, 15B:
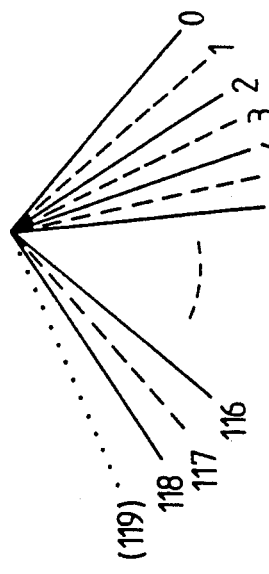
FIGS. 15(A) and 15(B) show the fourth example of the invention's color Doppler scanning pattern.

FIGS. 15(A) and 15(B) show a fourth example of a color Doppler scanning pattern according to this invention. FIG. 15(A) shows 120 rasters, addressed 0th to 118th and 1 dummy raster. For a B-mode scan, ultrasonic data are transmitted and received only 1 time for each raster for collecting B-mode image data. For a CFM scan, ultrasonic data are transmitted and received 16 times for each alternate raster (total 60 rasters) for collecting CFM image data. In FIG. 15(B), first, the 2nd and 0th rasters are alternately scanned 6 times each by CFM scan. Next, the 2nd raster is scanned 1 time by CFM scan, then the 0th raster is scanned 1 time by B-mode scan, then the 2nd raster is scanned 1 time by CFM scan, then 1st raster is scanned 1 time by B-mode scan, then the 2nd raster is scanned 1 time by CFM scan, then 2nd raster is scanned 1 time by B-mode scan, then 2nd raster is scanned 1 time by CFM scan, then 3rd raster is scanned 1 time by B-mode scan. Then the 2nd and 4th rasters are alternately scanned 6 times each by CFM scan. Then, as described above, all rasters are scanned by B-mode scan and CFM scan as shown in FIG. 15(B). Therefore, 30 rasters are scanned by CFM scan while 120 rasters (1 frame) are scanned by B-mode scan, and 2 frames (120×2 rasters) are scanned by B-mode scan while 1 frame (60 rasters) is scanned by CFM scan.

Figure 16:
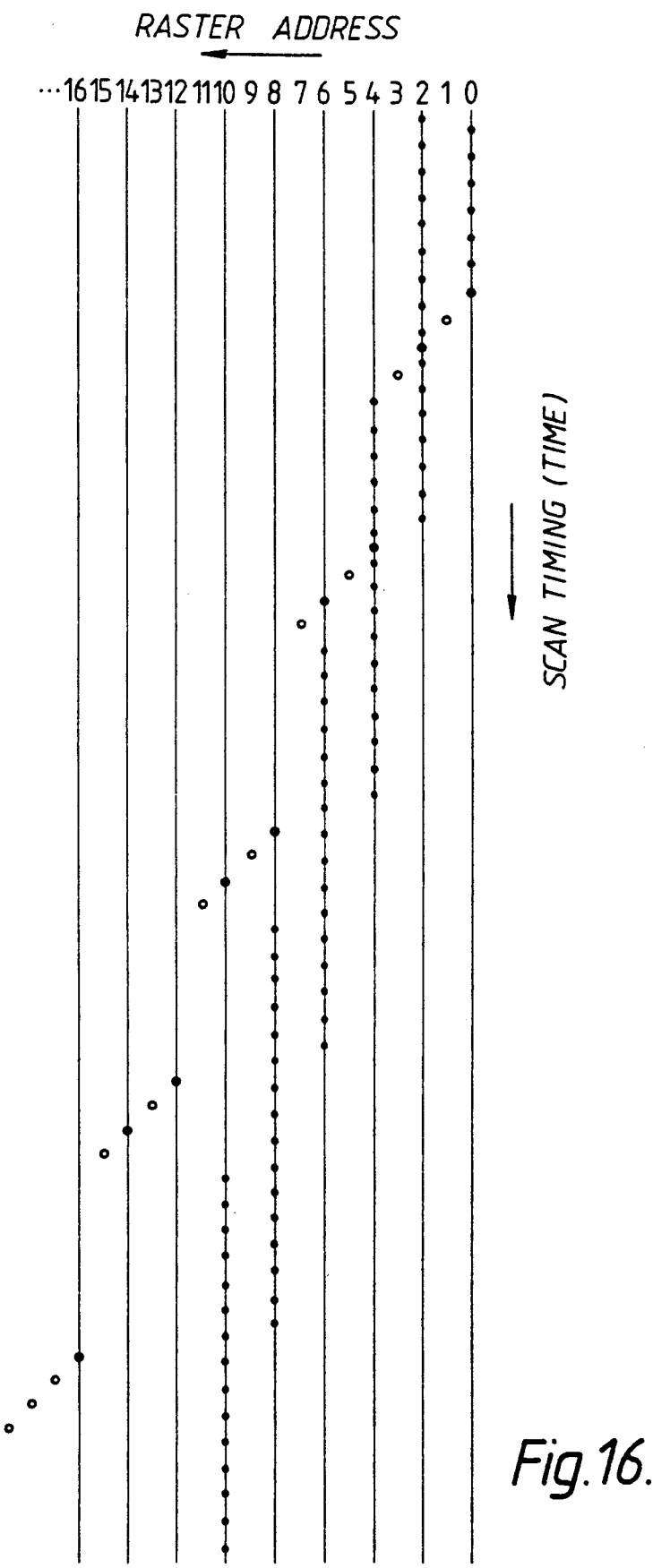
FIG. 16 shows the relationship between raster addresses and scanning timing for the fourth example of the invention's color Doppler scan.

This scanning method is called interleave scan, and a chart of this scan-timing and raster addresses are shown in FIG. 16. In FIG. 16, a black dot (●) shows a timing for CFM scanning, and a white dot (○) shows a timing for B-mode scanning. In this interleave scan, the CFM scanning rate for each raster is two times lower than the rate by scanning method in FIG. 12, therefore it can be detected two times slower velocity of blood flow than can be detected by the scanning method in FIG. 12. Then, in this interleave scan, it is equal for each raster that the period for correcting 16 data by CFM scan.

Thus, one frame of data for displaying a CFM image and a B-mode image is acquired. If the PRF for transmitting the ultrasonic pulse is 5 KHz, the B-mode scanning frame rate BFR4 and the CFM scanning frame rate CFR4 in this fourth embodiment are calculated as follows.

$$BFR4 = (5 \times 10^3)/(120 \times 1 + 30 \times 16) = 8.33 \text{ (frames / 1 second)}$$

$$CFR4 = (5 \times 10^3)/(60 \times 16 + 120 \times 2) = 4.17 \text{ (frames / 1 second)}$$

This means that the B-mode scanning frame rate BFR4 is about 2 times (=8.33/4.17) higher than the CFM scanning frame rate CFR4, and the BFR4 is about 1.8 times higher than the B-mode frame rate FR4 (=4.63) of the conventional color Doppler scan and the CFR4 is about 0.9 times higher than the CFM frame rate FR4 of the conventional color Doppler scan in FIG. 4. Therefore, realtime following ability for displaying B-mode image is 1.8 times improved from the conventional color Doppler scan. One interpolated CFM imaging frame, produced by DSC 26, is inserted between two scanned CFM imaging frames, and the CFM images are displayed on the scanned B-mode images on display 46.

Figures 17A, 17B:
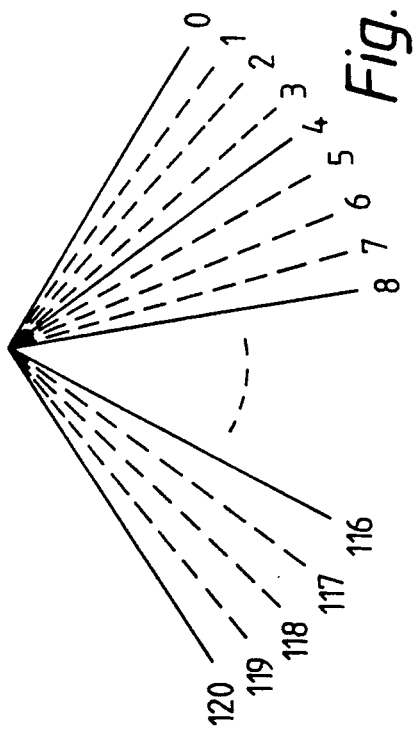
FIGS. 17(A) and 17(B) show the fifth example of the invention's color Doppler scanning pattern.

FIGS. 17(A) and 17(B) show a fifth example of a color Doppler scanning pattern according to this invention. FIG. 17(A) shows 124 rasters, addressed 0th to 120th and 3 dummy rasters (not shown). For a B-mode scan, ultrasonic data are transmitted and received 1 time for each raster for collecting B-mode image data. For a CFM scan, ultrasonic data are transmitted and received 16 times for each alternate 4 raster intervals (total 30 rasters) for collecting CFM image data. In FIG. 17(B), first, the 0th raster is scanned 1 time by B-mode scan, and then the 0th raster is scanned 1 time by CFM scan. Next, the 1st raster is scanned 1 time by B-mode scan, and then the 0th raster is scanned 1 time by CFM scan. Then alternately, as described above, the rasters are scanned by B-mode scan and CFM scan as shown in FIG. 17(B). Therefore, there are 124 CFM scans while 124 rasters (1 frame) are scanned by B-mode scan, and 30×16 rasters are scanned by the B-mode scan while 1 frame (30×16 rasters) are scanned by CFM scan. Thus, one frame of data for displaying CFM image and B-mode image is acquired. If the PRF for transmitting the ultrasonic pulse is 5 KHz, the B-mode scanning frame rate BFR5 and the CFM scanning frame rate CFR5 in this fifth embodiment are calculated as follows.

$$BFR5 = (5 \times 10^3)/(124 + 124) = 20.16 \text{ (frames / 1 second)}$$

$$CFR5 = (5 \times 10^3)/(30 \times 16 + 30 \times 16) = 5.21 \text{ (frames / 1 second)}$$

This means that the B-mode scanning frame rate BFR5 is about 3.9 times (=20.16/5.21) higher than the CFM scanning frame rate CFR5. In this scan, the CFM scanning rate for each raster is two times lower than the rate by scanning method in FIG. 12, therefore it can detect two times slower velocity of blood flow than could be detected by the scanning method illustrated in FIG. 12.

Figures 18A, 18B:
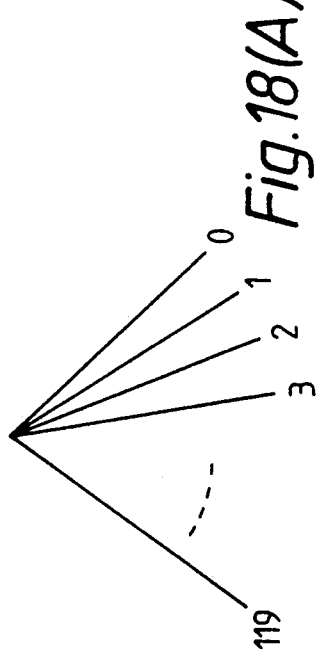
FIGS. 18(A) and 18(B) show the sixth example of the invention's color Doppler scanning pattern.

FIGS. 18(A) and 18(B) show a sixth example of a color Doppler scanning pattern according to this invention. FIG. 18(A) shows 120 rasters, addressed 0th to 119th. For a B-mode scan, ultrasonic data are transmitted and received only 1 time for each raster for collecting B-mode image data. For a CFM scan, ultrasonic data are transmitted and received 16 times for each raster (total 120 rasters) for collecting CFM image data. In FIG. 18(B), first, the 0th raster is scanned 1 time by B-mode scan, and then the 0th raster is scanned 16 times by CFM scan. Next, the 1st raster is scanned 1 time by B-mode scan, and then the 1st raster is scanned 16 times by CFM scan. Then alternately, as described above, the 2nd to the 119th rasters are scanned by B-mode scan and CFM scan in the first frame. Next, in the second frame, the 0th to the 119th rasters are scanned by B-mode scan only. Next, in the third frame, the 0th to the 119th rasters are alternately scanned 1 time each by B-mode scan and 16 times each scanned by CFM scan, as in the first frame. Thus, each frame of data is acquired. If the PRF for transmitting the ultrasonic pulse is 5 KHz, the B-mode scanning frame rate BFR6 and the CFM scanning frame rate CFR6 in this sixth embodiment are calculated as follows.

$$BFR6 = (5 \times 10^3)/(120 + 120 \times 16 + 120) \times 2 = 4.63 \text{(frames / 1 second)}$$

$$CFR6 = (5 \times 10^3)/(120 + 120 \times 16 + 120) = 2.31 \text{ (frames / 1 second)}$$

This means that the B-mode scanning frame rate BFR6 is 2 times higher than the CFM scanning frame rate CFR6, and the BFR6 is about 1.9 times higher than the B-mode frame rate FRI (=2.45) of the conventional color Doppler scan and the CFR6 is about equal to the CFM frame rate FR1 of the conventional color Doppler scan. Therefore, the realtime following ability for displaying a B-mode image is improved from the conventional color Doppler scan. Then, one interpolated CFM imaging frame, produced by DSC 26, is inserted between two scanned CFM imaging frames, and the CFM images are displayed on the scanned B-mode images on display 46.

Generally said, the color Doppler scan of this invention provided that the period for scanning N frames

*=2) by B-mode scan and the period for scanning M frame(s) ($1 <= M < N$) by CFM scan are equal.

Additional advantages and modifications will readily occur to those skilled in the art. Therefore, the invention in its broader aspects is not limited to the specific details, and representative devices, shown and described. Accordingly various modifications may be made without departing from the spirit or scope of the general, inventive concept as defined by the appended claims and their equivalents.

What is claimed is:

1. An ultrasonic diagnosis apparatus for displaying an ultrasonic image, which image is obtained by data from a plurality of rasters scanned by an ultrasonic imaging transducer, comprising:

transducer means;

B-mode scanning means for scanning each raster by controlling the transducer means such that the transducer means transmits an ultrasonic pulse and receives a reflected echo from each raster;

CFM scanning means for scanning each raster by controlling the transducer means such that the transducer means transmits plural ultrasonic pulses and receives plural reflected echoes from each raster;

B-mode imaging means for calculating an intensity data from the reflected echo scanned by the B-mode scanning means for each raster, and for producing a tomogram image for a frame from the intensity data calculated in a plurality of rasters;

CFM imaging means for calculating d Doppler shift data from the reflected echoes scanned by the CFM scanning means for each raster, and for producing a color flow mapping image for a frame from the Doppler shift data calculated in a plurality of rasters;

display means for displaying the color flow mapping image on the tomogram image; and scan controlling means for independently controlling a first scanning frame rate used by the B-mode scanning means for scanning a frame and a second scanning frame rate used by the CFM scanning means for scanning a frame, wherein the first scanning frame rate used by the B-mode scanning means for scanning a frame is higher than the second scanning frame rate used by the CFM scanning means for scanning a frame, and wherein when the CFM scanning means scans one frame, the B-mode scanning means scans more than one frame.

2. An apparatus according to claim 1, further comprising interpolating means for interpolating a frame of the color flow mapping image from data used to produce on earlier frame of the color flow mapping image.

3. An apparatus according to claim 2, wherein the display means alternately displays the color flow mapping image produced by the CFM imaging means and the interpolated color flow mapping image produced by the interpolating means.

4. An apparatus according to claim 1, wherein said scan controlling means controls the B-mode scanning and the CFM scanning in an interleave scanning pattern.

5. An apparatus according to claim 2, wherein said scan controlling means controls the B-mode scanning and the CFM scanning in an interleave scanning pattern.

6. An apparatus according to claim 3, wherein said scan controlling means controls the B-mode scanning and the CFM scanning in an interleave scanning pattern.

7. An ultrasonic diagnosis apparatus for displaying ultrasonic image, which image is obtained by data from a plurality of rasters scanned by an ultrasonic imaging transducer, comprising:

transducer means;

B-mode scanning means for scanning each raster by controlling the transducer means such that the transducer means transmits an ultrasonic pulse and receives a reflected echo from each raster;

CFM scanning means for scanning each raster by controlling the transducer means such that the transducer means transmits plural ultrasonic pulses and receives plural reflected echoes from each raster;

B-mode imaging means for calculating an intensity data from the reflected echo scanned by the B-mode scanning means for each raster, and for producing a tomogram image for a frame from the intensity data calculated in a plurality of rasters;

CFM imaging means for calculating a Doppler shift data from the reflected echoes scanned by the CFM scanning means for each raster, and for producing a color flow mapping image for a frame from the Doppler shift data calculated in a plurality of rasters;

display means for displaying the color flow mapping image on the tomogram image; and scan controlling means for independently controlling a period for scanning N frames ($N >= 2$) by the B-mode scanning means and a period for scanning M frame(s) ($1 <= M < N$) by the CFM scanning means so that the period for scanning N frames by the B-mode scanning means and the period for scanning M frame(s) by the CFM scanning means are equal.

8. An apparatus according to claim 7, further comprising interpolating means for interpolating a frame of the color flow mapping image from data used to produce on earlier frame of the color flow mapping image.

9. An apparatus according to claim 8, wherein the display means alternately displays the color flow mapping image produced by the CFM imaging means and the interpolated color flow mapping image produced by the interpolating means.

10. An apparatus according to claim 7, wherein said scan controlling means controls the B-mode scanning and the CFM scanning in an interleave scanning pattern.

11. An apparatus according to claim 8, wherein said scan controlling means controls the B-mode scanning and the CFM scanning in an interleave scanning pattern.

12. An apparatus according to claim 9, wherein said scan controlling means controls the B-mode scanning and the CFM scanning in an interleave scanning pattern.

* * * * *